United States Patent [19]  
Tibbetts et al.

[11] Patent Number: 4,920,211  
[45] Date of Patent: Apr. 24, 1990

[54] MUTATED ADENOVIRUS E1A GENE FOR E1A PROMOTER STIMULATION

[75] Inventors: Clark Tibbetts, Nashville, Tenn.; Pamela L. Larsen, Brookline, Mass.

[73] Assignee: Vanderbilt University, Nashville, Tenn.

[21] Appl. No.: 140,625

[22] Filed: Jan. 4, 1988

[51] Int. Cl.$^5$ .................. C12N 15/00; C12P 21/00; C07H 15/12
[52] U.S. Cl. .................. 536/27; 435/172.3; 435/235; 435/320; 435/69.1; 935/32; 935/27; 935/34; 935/36; 935/57
[58] Field of Search .................. 435/68, 70, 91, 172.3, 435/320, 235, 240.1, 240.2, 5; 536/27; 935/32, 27, 34, 36, 57

[56] References Cited

U.S. PATENT DOCUMENTS 4,755,630 10/1988 Tibbetts et al. .................. 435/68

OTHER PUBLICATIONS

Hearing, P., et al. (1985), Mol. Cell. Biol., 5:3214–3221.
Kosturko, L. D., et al. (1982), J. Virol., 43:1132–1137.
Larsen, et al., (1986), Virology 155:148–159.
Tibbetts, et al. (1986), J. Virol., 57:1055–1064.
Weeks, et al. (1983), Mol. Cell. Biol., 3:1222–1234.
Larsen, et al. (1987), Proc. Natl. Acad. Sci. U.S.A., 84:8185–8189.

Primary Examiner—Robin L. Teskin
Attorney, Agent, or Firm—Tilton, Fallon, Lungmus & Chestnut

[57] ABSTRACT

A functional mutated E1A gene of human adenovirus subgroup B:1 is provided which has a modified autorepression functional domain that is effective to express E1A products that stimulate without net repression of promoters controlling an E1A mutated gene.

12 Claims, No Drawings

MUTATED ADENOVIRUS E1A GENE FOR E1A PROMOTER STIMULATION

GRANT REFERENCE

This invention was developed in part under DHS Grant CA-34126, National Cancer Institute, U.S. Department of Health and Human Services.

FIELD OF INVENTION

The field of this invention is human adenovirus, their E1A genes and products, and the regulation of E1A gene expression.

BACKGROUND OF INVENTION

The control region of the human adenovirus genome and its relation to the E1A gene has been extensively studied. It is known that the protein products of the adenovirus E1A gene may act as positive and negative regulators of early viral gene expression, and that E1A products regulate at the transcriptional level. Sequences located 5' to the early viral regions contain sites which confer regulation by the E1A gene product, Weeks and Jones (1983). Positive and negative autoregulation of the adenovirus E1A gene transcription by E1A gene products has been reported. Tibbetts et al. (1986).

The E1A control region and E1A gene expression for adenovirus type 3 (Ad3) was further studied by Larsen, et al. (1986). They reported a defective mutant of Ad3, designated Ad 3 hr 15, which failed to propagate on normally permissive A549 cells, but had greater infectivity than wild-type Ad3 in the adenovirus type 5 (Ad5) DNA-transformed 293 cells. Investigation of the genomic alteration revealed that the Ad 3 hr 15 mutant had two short tandem duplications of viral DNA sequences near its left end, 5' to the E1A gene. Marker rescue experiments with plasmid-cloned left end DNA sequences of Ad3 indicated that the duplications 5' to E1A were responsible for the Ad 3 h 15 defect, and the E1A gene of the variant was functional. The E1A gene promoter with the reiterated sequence provides a transcriptional control element adapted for regulation of gene expression in animal cells, as described in the co-pending application of Tibbetts et al., Ser. No. 897,042, filed Aug. 15, 1986, now patent 4,775,630.

As described by Larsen et al. (1986) and in the cited co-pending application, the Ad3 hr15 promoter for the E1A gene responds in trans to Ad3 E1A wild-type products to repress the expression of the E1A gene or other gene under its control. The response to adenovirus type 5 (Ad5) E1A wild-type gene products enhances expression of the controlled gene.

Since the duplicated sequence of this promoter makes it highly sensitive to both positive and negative effects of E1A gene products, it is important to regulate the promoter. Prior to the present invention, it was not known how to produce Ad3 E1A gene products which have a net stimulatory action on the Ad 3 h 15 promoter.

SUMMARY OF INVENTION

By high multiple passage of Ad 3 h 15 virus in permissive 293 cells, followed by plaque assay on non-permissive A549 cells, spontaneous mutations were recovered in the wild-type E1A gene of the Ad 3 hr 15 virus. These isolated virus strains were phenotype revertants of Ad 3 hr 15. The E1A genes of the revertants have deletion mutations occurring in the DNA "spacer" region between the conserved domains II and III of Kimmelman et al. (1985). The deletions varied in length from 20 to 100 base pairs (bp). Selected revertants having 27 to 69 bp deletions were found to contain functional E1A genes which produced E1A products that differed significantly from the E1A products of the wild-type Ad3 gene. The modified gene products were found to be capable of producing a stimulatory effect on the sensitive promoter of Ad 3 hr 15 with the reiterated DNA sequences. When the Ad 3 hr 15 promoter was suppressed by wild-type Ad3 E1A gene products, the suppression could be overcome by the modified gene products. In general, the modified E1A products act positively, stimulating in trans without any net repression of promoters controlling the E1A genes of adenovirus subgroup B:1.

Sequence analysis of the mutated E1A genes of the Ad 3 h 15 virus identified an autorepression functional domain which had been previously regarded as a "spacer" sequence between the conserved II and III domains. With reference to numerical sequencing, of wild-type Ad3, this autorepression domain is located between nucleotides 956 and 1024. That region as well as the entire E1A gene is highly homologous for all human adenovirus subgroup B:1, which includes Ad3, Ad7, Ad16, and Ad21. The subgroup B:1 adenoviruses include the same autorepression functional domain which functions to produce E1A gene products that are inhibitory to the promoter in trans, that is, net balance of the autoregulation is negative rather than positive.

Summarizing, the present invention provides a functional mutated E1A gene of human adenovirus subgroup B:1 having a modified autorepression functional domain which is effective to express E1A products that stimulate without net repression of promoters controlling the E1A mutated gene.

DETAILED DESCRIPTION

The mutated E1A gene of this invention can be prepared from the Ad3 mutant virus designated Ad 3 hr 15. The mutant has been deposited with The American Type Culture Collection, Rockville, MD, under Accession No. VR 2197, and is now permanently available due to issuance of U.S. Pat. No. 4,775,630. The Ad 3 h 15 virus can be replicated on 293 cells, a cell line derived from human embryonic kidney cells transformed by DNA of human adenovirus type 5 (Ad5). The Ad 3 hr 15 virus are employed for high multiple infection of A549 cells, a cell line derived from a human lung carcinoma equivalent to HeLa or KB cells for growth of adenovirus type 3. The A549 cells are normally non-permissive for Ad 3 h 15 virus. After the high multiple infection, viral revertant plaques are isolated from the 549 cells. The revertants are propagated in normally-permissive cells for Ad3 virus and are characterized biologically for growth. A revertant mutated virus which produces E1A products stimulatory to the Ad3 h15 promoter is selected. The mutants are further characterized by DNA sequencing to confirm that they have the preferred deletions between nucleotides 956 and 1024 of wild-type Ad3. The preferred region for the deletions is from nucleotide 974 to nucleotide 1000 (referenced to wild-type Ad3).

Stated in greater detail, the preparation of mutated E1A genes of this invention involves the following steps:

(1) Serial, high multiplicity passage of Ad 3 hr 15 lysates on 293 cells. Ex.: 3 to 5 passages, infecting plates with 0.1 ml lysate per $10^7$ cells (lysate is resuspended infected 293 cells, about $10^7$ cells/ml in 0.10 m Tris, pH 7.5; lysates subjected to freeze-thaw and sonication before use as inocula).

(2) Infect fresh cultures of A549 cells as for 293 cells described above. Process lysate (after 2-3 weeks infection). Use this first passage A549 lysate for isolation of revertants as in steps below.

(3) Plaque titration of high passage lysate on A549 cells. Select plaques of typical wild-type Ad3 appearance (1 to 3 mm diameter after 10-20 days). A background of "microplaques" may appear. Repeat of plaque purification of selected plaques is advised.

(4) Test (by plaque-assay) for equal or preferential growth of candidate revertant plaques on A549 cells compared to 293 cells.

(5) Prepare virus samples from infected A549 cells ($10^8$ cells-10 plates should be sufficient). Purify virions, extract DNA and analyze by restriction using standard procedures (see Larsen et al., 1986).

(6) Identify E1A deletion revertants by altered size of restriction fragments. Confirm by DNA sequence analysis.

The genome of adenovirus type 3 (Ad3) is about 36,000 base pairs (bp) of double-stranded linear DNA. The E1A gene and its regulatory sequence are in the leftmost 1600 bp. The entire sequence up to the Bgl II restriction site at nucleotide 1564 for Ad3 is highly homologous (98% or greater) with the corresponding sequences of other subgroup B:1 adenovirus. This serotype homology has been indicated in prior reports, including Tibbetts (1977), and Kosturko, et al. (1982).

The subgroup B:1 homology extends to the autorepression functional domain, which was discovered and determined for the first time in the development of the present invention. With reference to the numbering of the Ad3 serotype, the autorepression functional domain is between nucleotides 956 and 1024. The corresponding highly homologous regions of the other serotypes of subgroup B:1 include those of Ad7, Ad16, and Ad21. The autorepression domain is between the BamH I restriction site at nucleotide 745 (wild-type Ad3) and the Hind III site at bp 1384. These restriction sites permit the use of endonuclease enzymes to cleave segments of the Ad3 H15 revertants (viz. bp 745 to bp 1384) containing the mutated E1A gene. These cleavage segments can be inserted in any of the subgroup B:1 adenovirus. The mutated E1A gene can thereby be utilized for control of wild-type E1A gene promoters, or mutated promoters such as the Ad3 hr15 promoter.

The results of sequencing analysis of wild-type Ad3 from 1 to 1569 bp are presented in the following Diagrams A and B, which show both DNA strands. The letters A, T, G, and C have the standard meanings of adenine, thyamine, guanine, and cystosine. Restriction sites are indicated, respectively, at bp 745, bp 1384, and bp 1564.

DIAGRAM A
(Wild-type Ad3 Sequence)

1: CTATCTATATAATATACCTTAAGATGGAATGGTGCCAACATGTAAATGAGGTAATTTAAA :60
   GATAGATATATTATATGGAATTCTACCTTACCACGGTTGTACATTTACTCCATTAAATTT

61: AAAGTGCGCGCTGTGTGGTGATTGGCTGCGGGGTTAACGGCTAAAAGGGGCGGCGCGACC :120
    TTTCACGCGCGACACACCACTAACCGACGCCCCAATTGCCGATTTTCCCCGCCGCGCTGG

121: GTGGGAAAATGACGTGACTTATGTGGGAGGAGTTATGTTGCAAGTTATTACGGTAAATGT :180
     CACCCTTTTACTGCACTGAATACACCCTCCTCAATACAACGTTCAATAATGCCATTTACA

181: GACGTAAAACGAGGTGTGGTTTGAACACGGAAGTAGACAGTTTTCCCACGCTTACTGACA :240
     CTGCATTTTGCTCCACACCAAACTTGTGCCTTCATCTGTCAAAAGGGTGCGAATGACTGT

241: GGATATGAGGTAGTTTTGGGCGGATGCAAGTGAAAATTCTCCATTTTCGCGCGAAAACTA :300
     CCTATACTCCATCAAAACCCGCCTACGTTCACTTTTAAGAGGTAAAAGCGCGCTTTTGAT

301: AATGAGGAAGTGAATTTCTGAGTCATTTCGCGGTTATGCCAGGGTGGAGTATTTGCCGAG :360
     TTACTCCTTCACTTAAAGACTCAGTAAAGCGCCAATACGGTCCCACCTCATAAACGGCTC

361: GGCCGAGTATACTTTGACCGTTTACGTGGAGGTTTCGATTACCGTGTTTTTCACCTAAAT :420
     CCGGCTCATATGAAACTGGCAAATGCACCTCCAAAGCTAATGGCACAAAAAGTGGATTTA

421: TTCCGCGTACGGTGTCAAAGTCCTGTGTTTTTACGTAGGTGTCAGCTGATCGTCAGGGTA :480
     AAGGCGCATGCCACAGTTTCAGGACACAAAAATGCATCCACAGTCGACTAGCAGTCCCAT

481: TTTAAACCTGACGAGTTCCGTCAAGAGGCCACTCTTGAGTGCCAGCGAGAAGAGTTTTCT :540
     AAATTTGGACTGCTCAAGGCAGTTCTCCGGTGAGAACTCACGGTCGCTCTTCTCAAAAGA

541: CCTCCGCGCCGCAAGTCAGTTCTGCGCTTTGAAAATGAGACACCTGCGCTTCCTGCCACA :600
     GGAGGCGCGGCGTTCAGTCAAGACGCGAAACTTTTACTCTGTGGACGCGAAGGACGGTGT

601: GGAGGTTATCTCCAGTGAGACCGGGATCGAAATACTGGAGTTTGTGGTAAATACCCTAAT :660
     CCTCCAATAGAGGTCACTCTGGCCCTAGCTTTATGACCTCAAACACCATTTATGGGATTA

661: GGGAGACGACCCGGAACCGCCAGTGCAGCCTTTCGATCCACCTACGCTGCACGATCTGTA :720
     CCCTCTGCTGGGCCTTGGCGGTCACGTCGGAAAGCTAGGTGGATGCGACGTGCTAGACAT 745 (BamH I)
                      |
721: TGATTTAGAGATAGACGGGCCGGAGGATCCCAATGAGGAAGCTGTGAATGGGTTTTTTAC :780
     ACTAAATCTCTATCTGCCCGGCCTCCTAGGGTTACTCCTTCGACACTTACCCAAAAAATG

-continued
DIAGRAM A
(Wild-type Ad3 Sequence)

```
781: TGATTCTATGCTGCTAGCTGCTGATGAAGGATTGGACATAAACCCTCCTCCTGAGACACT :840
     ACTAAGATACGACGATCGACGACTACTTCCTAACCTGTATTTGGGAGGAGGACTCTGTGA
```

DIAGRAM B
(Wild-type Ad3 Sequence)

```
841: TGTTACCCCAGGGGTGGTTGTGGAAAGCGGCATAGGTGGGAAAAAATTGCCTGATCTGGG :900
     ACAATGGGGTCCCCACCAACACCTTTCGCCGTATCCACCCTTTTTTAACGGACTAGACCC
```

```
                                                                ↓
901: AGCAGCTGAAATGGACTTGCGTTGTTATGAAGAGGGTTTTCCTCCCAGTGATGATGAAGA :960
     TCGTCGACTTTACCTGAACGCAACAATACTTCTCCCAAAAGGAGGGTCACTACTACTTCT
                                                                |
                                                            956 (dl13)
```

```
               ↓                              ↓
961: TGGGGAAACTGAGCAGTCCATCCATACCGCAGTAAATGAGGGAGTAAAAGCTGCCAGCGA :1020
     ACCCCTTTGACTCGTCAGGTAGGTATGGCGTCATTTACTCCCTCATTTTCGACGGTCGCT
               |                              |
           974 (dl7)                       1000 (dl7)
```

```
     ↓
1021: TGTTTTTAAGTTGGACTGTCCGGAGCTGCCTGGACATGGCTGTAAGTCTTGTGAATTTCA :1080
      ACAAAAATTCAACCTGACAGGCCTCGACGGACCTGTACCGACATTCAGAACACTTAAAGT
      |
   1024 (dl13)
```

```
1081: CAGGAATAACACTGGAATGAAAGAACTATTGTGCGTCCTTTGCTATATGAGAATGCACTG :1140
      GTCCTTATTGTGACCTTACTTTCTTGATAACACGCAGGAAACGATATACTCTTACGTGAC
```

```
1141: CCACTTTATTTACAGTAAGTGTATTTAAGTGAAATTTAAAGGAATAGTGTAGCTGTTTAA :1200
      GGTGAAATAAATGTCATTCACATAAATTCACTTTAAATTTCCTTATCACATCGACAAATT
```

```
1201: TAAACTGTTGAATGGTAGATTTATGTTTTTTCTTGCGATTTTTTGTAGGTCCTGTGTCT :1260
      ATTTGACAACTTACCATCTAAATACAAAAAAGAACGCTAAAAAACATCCAGGACACAGA
```

```
1261: GATGATGAGTCACCTTCTCCTGATTCAACTACCTCACCTCCTGAAATTCAGGCGCCCGCA :1320
      CTACTACTCAGTGGAAGAGGACTAAGTTGATGGAGTGGAGGACTTTAAGTCCGCGGGCGT
```

```
1321: CCTGCAAACGTATGCAAGCCCATTCCTGTGAAGCCTAAGCCTGGGAAACGCCCTGCTGTG :1380
      GGACGTTTGCATACGTTCGGGTAAGGACACTTCGGATTCGGACCCTTTGCGGGACGACAC
```

```
         1384 (Hind III)
             |
1381: GATAAGCTTGAGGACTTGTTGGAGGGTGGGGATGGACCTTTGGACCTTAGTACCCGGAAA :1440
      CTATTCGAACTCCTGAACAACCTCCCACCCCTACCTGGAAACCTGGAATCATGGGCCTTT
```

```
1441: CTGCCAAGGCAATGAGTGCCCTGCAGCTGTGTTTATTTAATGTGACGTCATGTAATAAAA :1500
      GACGGTTCCGTTACTCACGGGACGTCGACACAAATAAATTACACTGCAGTACATTATTTT
```

```
1501: TTATGTCAGCTGCTGAGTGTTTTATTACTTCTTGGGTGGGGACTTGGATATATAAGTAGG :1560
      AATACAGTCGACGACTCACAAAATAATGAAGAACCCACCCCTGAACCTATATATTCATCC
```

```
       1564 (Bgl II)
           |
1561: AGCAGATCT                                                    :1569
      TCGTCTAGA
```

(1) bp 281–340 these 60 bp contain the E1A promoter-proximal enhancer element. The DNA sequence is duplicated in tandem in the promoter of the mutant Ad3hr15.
5'-GAGGAAGTGAA-3' core DNA sequence of the
|            enhancer element
bp 304

(2) The TATA element of the E1A promoter
5'-TATTTAAA-3'
|
bp 479

(3) The transcription start site for the E1A gene. The adenosine transcribed from bp 511 is capped.

(4) The start codon for translation of E1A mRNA's
5'-ATG-3'
|
bp 575

(5) The BamH I restriction site, located in the E1A gene's 5' exon
5'-GGATCC-3'
|
bp 745

-continued (6) The 12S mRNA splice junction
5'-TGGCTGTCCT-3'
   /        \
bp 1061    bp 1255

The 13S mRNA splice junction

5'-TTACAGTCCT-3'
   /        \
bp 1154    bp 1255

(7) The Hind III restriction site, located in the E1A gene's 3' exon
5'-AAGCTT-3'
   |
   bp 1384

(8) The E1A gene's translational stop codon
5'-TGA-3'
   |
   bp 1453

(9) The 3' mRNA polyadenylation signal
5'-AATAAA-3'
   |
   bp 1494
Polyadenylation at bp 1511 (T, U in the RNA)

(10) The Bgl II restriction site
5'-AGATCT-3'
   |
   bp 1564

The largest deletions in a viable revertant thus far isolated is 69 bp (23 codons), the deletion starting with bp 956 and ending with bp 1024. As indicated in Diagram B, the vertical arrows represent cleavage sites for the 69 bp deletion, which revertant virus was designated Ad 3 h 15-dl13. The smallest deletion in a viable mutant thus far isolated has a deletion of 27 bp (9 codons) starting at bp 974 and ending at bp 1000. That deletion is also indicated on Diagram B, and the cleavage sites are marked by the vertical arrows. The 27 bp deletion reversion virus has been designated Ad 3 h 15-dl7. The dl7 and dl13 revertants are being maintained in the laboratory of Dr. Clark Tibbetts, Department of Microbiology, School of Medicine, Vanderbilt University, Nashville, Tenn.

The dl7 and dl13 revertant viruses also contain the duplicate Ad 3 h 15 regulator for the E1A gene. This domain comprises a transcriptional regulator followed in tandem by a duplicate thereof. The response of this regulator to Ad3 E1A wild-type products represses expression of the E1A gene. The response to the E1A products of the mutated gene of this invention, however, enhances expression of the mutated E1A gene. This combination of duplicated promoter and mutated gene can be utilized effectively to provide E1A gene products which have a positive or stimulatory effect on wild-type promoters of the subgroup B:1 serotypes, as well as on the mutated Ad 3 h 15 promoter.

A sequence analysis for the bp region 1 to 722 of Ad 3 h 15 is shown in Diagram C. Only one nucleotide for each base pair is shown.

DIAGRAM C
(Ad 3hr 15 Sequence)

(1) ATACCTT AAGATGGAAT GGTGCCAACA TGTAAATGAG (37)

(56)                          (83)
                                |                             |
(38) GTAATTTAAA AAAGTGCGCG CTGTGTGGTG ATTGGCTGCG GGGTTAAC (85)
                           30 bp
                                                  Hpa I

(86) CG CTGTGTGGTG ATTGGCTGCG GGGTTAAC (115)
        30 bp
                                    Hpa I (116) GG CTAAAAGGGG CGGCGCGACC GTGGGAAAAT GACGTGACTT ATGTGGGAGG (167)

(168) AGTTATGTTG CAAGTTATTA CGGTAAATGT GACGTAAAAC GAGGTGTGGT (217)

(218) TTGAACACGG AAGTAGACAG TTTTCCCACG CTTACTGACA GGATATGAGG (267)

(298)
                                          |
(268) TAGTTTTGGG CGGATGCAAG TGAAAATTCT CCATTTTCGC GCGAAAACTA (307)

(308) AATGAGGAG TGAATTTCTG AGTCATTTCG CGGTTATGCC (374)
                         60 bp (348) CCATTTTCGC GCGAAAACTA (367)

(406)
                                                              |
(368) AATGAGGAAG TGAATTTCTG AGTCATTTCG CGGTTATGCC AGGGTGGAGT (417)
                         60 bp (418) ATTTGCCGAG GGCCGAGTAG ACTTTGACCG TTTACGTGGA GGTTTCGATT (467)

(468) ACCGTGTTTT TCACCTAAAT TTCCGCGTAC GGTGTCAAAG TCCTGTGTTT (517)

(518) TTACGTAGGT GTCAGCTGAT CGTCAGGGTA TTTAAACCTG ACGAGTTCCG (567)

(568) CTAAGAGGCC ACTCTTGAGT GCCAGCGAGA GAGTTTTCT CCTCCGCGCC (617)

(643)
                                |
(618) GCAAGTCAGT TCTGCGCTTT GAAATGAGA CACCTGCGCT TCCTGCCACA (667)

-continued
DIAGRAM C
(Ad 3hr 15 Sequence)

(668) GGAGGTTATC TCCAGTGAGA CCGGGATCGA AATACTGGAG TTTGTGGTAA (717)

(718) ATACC (722)

As shown in Diagram C, two tandem repetitions of 60 bp (nucleotides 298-347 and 348-406; double underscoring) are found near the left end of Ad 3 h 15 DNA. This is the region which was shown by the marker rescue to alter regulation of the E1A gene. The 30 bp duplications (nucleotides 56-85 and 86-115; single underscoring) are in the inverted terminal repeat region (ITR), and are not required for effective Ad 3 h 15 phenotype regulation. The larger repeats of 60 bp in tandem are the sequences responsible for the Ad 3 h 15 altered regulation. Shorter fragments containing the 60 bp tandem enhancer sequences can be prepared from the Ad 3 h 15 plasmid deposited under ATCC Accession No. 53156.

The wild-type Ad3 autorepression region is shown separately below in Diagram D as a basis for further discussion of this domain.

originally from the American Type Culture Collection and have been propagated as described in other reports from this laboratory (1, 8, 13–15). The isolation and characterization of the host range, defective mutant Ad 3 hr 15, was recently described by Larsen et al. (1986). The mutant can only be propagated by infection of 293 cells and is defective for E1A transcription and growth in A549 cells. Virions for isolation of DNA or for inoculation of cell cultures were extracted from infected cells and purified by three consecutive centrifugations in CsCl equilibrium density gradients (Ti75 rotor, 40,000 rpm, 4° C., 18 hr). Concentrations of virus preparations were estimated by dilution of an aliquot in 0.5% sodium lauryl sulfate solution (to lyse the virus and reduce light scattering) and determination of optical density at 260 nm, using the relation 1.0 $A_{260} = 1.0 \times 10^{12}$ virions per ml.

DIAGRAM D
(Wild-Type Ad3 Autorepression Region)

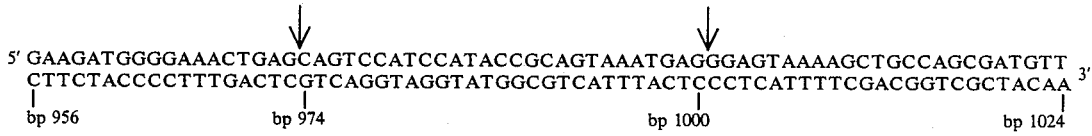

With reference to Diagram D, it is the DNA segment from bp 956 to bp 1024 which is missing in Ad 3 h 15-dl13, and the DNA segment from bp 974 to bp 1000 which is missing in Ad3 h15-dl7. While deletions are the preferred means of modifying the E1A products produced by the gene, other modifications of the autorepression region can be made which will achieve the same result; namely, expression of E1A gene products that stimulate in trans without net repression of the promoter controlling the E1A gene. Such mutations in the autorepression region can include insertions, or substitutions of DNA sequences, which like the deletions neither terminate nor shift the translational reading frame. Since the mutated E1A gene must be functional, the modifications must be in frame, whether they comprise deletions, insertions, or substitutions.

The basis of the present invention can be more fully understood from the following experimental examples.

EXPERIMENTAL EXAMPLES

Materials and Methods

Cells and Viruses

Cultures of 293 cells, human embryonic kidney cells transformed by DNA of human adenovirus type 5, were obtained from Dr. T. Shenk (Princeton University). The A549 cell line, derived from a human lung carcinoma and equivalent to HeLa or KB cells for growth of adenovirus type 3 or type 5, was obtained from the American Type Culture Collection. Monolayer cultures of these cells were maintained in Dulbecco's modified Eagle's medium with 10% calf serum as described previously (8). Human adenovirus type 5, strain adenoid 6, and adenovirus type 3, strain G.B., were obtained Isolation of revertants of Ad3 hr15

Purified virions of Ad3 hr15 (from infected 293 cell cultures) were used to infect A549 cell cultures at 1250 particles per cell. Cells, debris and media from this passage of the virus were collected two weeks after infection then sonicated and cleared by low speed centrifugation, 2000 rpm for 5 min. The supernatant was then used as inoculum for a second passage on fresh cultures of A549 cells. Plaque titration (on A549 cells) of the cleared lysates from the first and second passages yielded plaques, most of which were similar to those of wild type Ad3: 0.5 to 5.0 mm in diameter at 10 to 14 days after infection. At low dilutions of the first lysate, a background of pinpoint-sized "microplaques" appeared, typical of local, non-productive effects seen in high multiplicity infections of A549 cells by Ad3 hr15. The second lysate showed few of the "microplaques" at low dilution, however, there did appear several exceptionally large plaques (exceeding 10 mm diameter) not typical of wild type Ad3. In each lysate the numbers of the wild type-sized and the large plaques were proportional to dilution, suggesting single-hit infection kinetics. Forty-five independent revertant plaques were picked from the first and second lysate infections for the further characterization described in this report. Passage of these revertant viruses on A549 cells led to rapid, adenovirus type cytopathic effects and yielded large quantities of virus.

DNA, Enzymes, and Restriction/Sequence Analysis

Restriction enzymes, and other enzymes for DNA analysis were obtained. DNA fragments of restriction digests were separated by electrophoresis in 1% agarose slab gels with 0.5 ug/ml ethidium bromide for detection of DNA by fluorescence. DNA fragments (Hpa I, bp 95 to Bgl II, bp 1565) from the E1A genes of the revertant viruses were subcloned into the pEMBL 18 plasmid vector, prior to DNA sequence determination. The recombinant DNA was cleaved with BamH I, then 3' end-labeled using alpha $^{32}$P-dCTP together with unlabeled dATP, dGTP, dTTP and E. coli DNA polymerase I, Klenow fragment. Then Hind III was used for secondary restrictions in order to segregate the labeled ends prior to the chemical cleavage protocols of Maxam-Gilbert (1980).

Northern Blot Analysis of RNA from Infected Cells

Cultures of A549 or 293 cells were infected with freshly prepared, three times CsCl-banded adenovirus at 2000 particles per cell. Coinfections with two different adenoviruses were inoculated at 1000 particles of each virus type per cell. RNA was extracted at 3, 6, 9 and 20 hours after infection by use of guanidinium thiocyanate and centrifuged through a 5.7 m CsCl cushion (SW 41 rotor, 27000 rpm, 15° C., 16 hr). Northern hybridization analysis was performed following electrophoresis of RNA samples in formaldehyde-agarose gels, 10 ug RNA per track. The gels were blotted to Gene-Screen ™ (DuPont), hybridized with nick-translated plasmid DNA bearing Ad5 or Ad3 E1A genes, then exposed for autoradiography. Details of the entire procedure, including descriptions of Ad3 and Ad5 E1A-specific DNA probes have been reported earlier. (See Tibbetts, et al. (1986)).

DISCUSSION OF RESULTS

Revertants of Ad3 hr15

The physical map of the Ad3 E1A gene shown in FIG. 1 is very similar to maps of the more familiar subgroup C adenoviruses Ad2 and Ad5. The early E1A gene transcripts differ only by the length of intron removed. Their translation products share common amino- and carboxy-terminal peptide sequences. The defective mutant Ad3 hr15 has two short tandem DNA repetitions shown as inserts above the genome map in FIG. 1. The left duplication (bp 69–98) is not thought to be associated with the defective phenotype of the mutant. The longer repetition (bp 281–340) duplicates a region spanning the E1A promoter-proximal ("−200") enhancer core element identified in Ad5 by Hearing and Shenk (1985). This enhancer core DNA sequence is identical to the Ad3 and Ad5 genomes. Marker rescue experiments confirmed that the defective lesion of Ad 3 hr 15 is located left of the Pvu II restriction site, bp 465 (8).

The Ad 3 hr 15 mutant is remarkably defective and can only be propagated in the 293 cell line which provides E1A gene products of the heterologous adenovirus type 5. Although A549 cells are normally permissive for growth of Ad3 or Ad5, they do not support growth of the mutant Ad 3 hr 15 virus. This provided an opportunity to select for phenotypic revertants of Ad 3 hr 15 by high multiplicity (1250 particles per cell) infection of A540 cells. Lysates of such infected cell cultures were subjected to plaque titration on A549 cells for isolation of candidate revertant viruses. DNA purified from revertant virion preparations was characterized by DNA restriction analysis. There appeared to be no change in the size of the left end BamH I fragments in the revertant DNA digests, compared to Ad 3 hr 15. However, each of the phenotypic revertants was found to have incurred a small deletion of DNA in the region between the left BamH I and Hind III restriction sites. These revertant-specific E1A deletions varied from about 20 bp to 100 bp in length. Other restriction fragment size changes were noted among the 45 revertants that were screened, but none of these was consistently associated with the reverted growth phenotype. Thus reversion of the defective growth phenotype of Ad 3 hr 15 resulted from second site deletions in the E1A gene, rather than by alteration of the duplicate enhancer structure of the Ad 3 hr 15-type E1A promoter. The infectivity of revertants such as dl 7 and dl 13 was several orders of magnitude greater in A549 cells than the infectivity of mutant Ad 3 hr 15. The infectivity of these revertants in 293 cells was found to be similar to that of the mutant Ad 3 hr 15, about 2 to 3 times higher than for wild type Ad3 in A549 cells.

Physical Mapping of DNA from Revertant Viruses

Revertants dl 7 (Ad 3 hr 15-dl 17) and dl 13 (Ad 3 hr 15-dl 13) closely resemble the overall genotype of the Ad 3 hr 15 mutant from which they originated, except for their E1A gene deletions. Partial digestion restriction analysis of revertant viral DNA preparations further delimited the location of the deletions to the interval between the Pvu II (bp 908) and Alu I (bp 1111) restriction sites in the Ad3 E1A gene. Maxam-Gilbert DNA sequence analysis (cited above) defined these revertant deletions, aligned with the sequence of Ad3 DNA (a) from bp 950 to bp 1030 below. Translated amino acids are shown between (a) and (b).

```
950
(a) GATGATGAAGATGGGGAAACTGAGCAGTCCATCCATAC
     D   D   E   D   G   E   T   E   Q   S   I   H   T
(b) GATGATGAAGATGGGGAAACTGAG-----------------
(c) GATGAT----------------------------------

1030
CGCAGTAAATGAGGGAGTAAAAGCTGCCAGCGATGTTTTTAAG
  A   V   N   E   G   V   K   A   A   S   D   V   F   K
---------------GGAGTAAAAGCTGCCAGCGATGTTTTTAAG
------------------------------------------TTTAAG
```

Revertant dl 7 (b) deleted 27 base pairs, bp 974 to 1000 inclusive (Ad3 nucleotide numbers) and revertant dl 13 (c) deleted 69 base pairs, bp 956 to 1024 inclusive. These overlapping deletions thus maintained the translational reading frame, removing 9 or 23 codons from a region which is common to the 5' exons of 12S and 13S Ad3 E1A mRNA species.

Restored Capacity for E1A Gene Expression by Revertants

The results of Northern blot analysis demonstrated E1A gene expression by wild type Ad5 and Ad3 and the transcriptional defect of the Ad 3 hr 15 promoter. Wild type Ad3 expresses its E1A gene at earlier times after infection and with much greater levels of mRNA in infected A549 cells than does Ad5. E1A transcription by the mutant Ad 3 hr 15 is almost completely blocked in A549 cells. This minute signal is perhaps associated with events that eventually lead to the appearance of non-productive "microplaques" following such high multiplicity infections by the mutant virus.

The blocked transcription of the Ad 3 hr 15 E1A gene appears to be relaxed in cells which concomitantly express the Ad5 E1A gene. The Ad 3 hr 15-infected 293 cells accumulated abundant Ad3-type E1A transcripts after a delay of several hours similar to that for Ad3 infected 293 cells. By 9 hours after infection, however, the Ad 3 hr 15-infected 293 cells show more than E1A mRNA do wild-type Ad3-infected 293 cells. Ad3 hr5 also shows transcription of its E1A gene in cells coinfected with Ad5. In these cells, however, the appearance of the mutant's E1A transcripts is so late in the coinfection that the splicing appears to be specific for generation of the late 9S form of the mRNA.

A549 cells infected by the revertant dl 7 yielded even higher levels of its E1A mRNA species than observed for wild type Ad3. In another experiment, A549 cells were coinfected with Ad5 and the dl 7 revertant. RNA from the coinfected cells was separately analyzed using Ad5- or Ad3-specific E1A probe DNA. The levels of the revertant's E1A mRNA (detected with Ad3 probe) at different times after the coinfection were similar to the mRNA in cells infected by dl 7 virus alone. Ad5-E1A mRNA was also detected in these coinfected A549 cells. Although these Ad5 transcripts were at somewhat lower levels than in cells infected by Ad5 alone, there was no apparent delay in their appearance after infection. Coinfection experiments with Ad5 and Ad 3 hr 15-dl 13 led to similar results as with dl 7 and Ad5. These results contrast with those reported previously (Tibbetts et al., 1986) that wild type Ad3 virus completely represses expression of Ad5 E1A under these coinfection conditions.

PLASMID EXAMPLE

The mutated E1A gene of the type we describe for the Ad 3 hr 15 revertants can easily be constructed into plasmid form. Such plasmids have been constructed in this laboratory and used for expression of the mutant E1A genes in transfected Hela cells. The following procedure is an example which places the mutated E1A gene under control of the wild-type Ad3E1A promoter. Similar constructions can use the Ad 3 hr 15 E1A promoter for control of the mutant E1A gene expression.

Plasmid pCT132 (Kosturko et al., *J. Virol.*, 43, 1132–1137, 1982) is linearized with Bam HI.

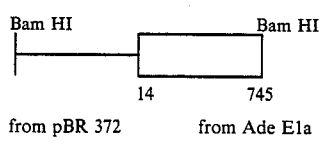

The DNA purified from the revertant virus (which has an altered E1A gene) is restricted with Bgl II and the "K" fragment (about 1560 bp) is isolated after agarose gel electrophoresis. This fragment is restricted with Bam HI (at bp 745) and the fragment (Bam HI (745) to Bgl II (1564)) is ligated to the Bam HI linearized vector (pCT 132) above. Bam HI and Bgl II generate identical 5' overhanging sequences and their restriction fragments ligate interchangeably. The ligation mixture is transformed into *E. coli* cells (Ampicillin selection). Individual clones are screened by restriction digests and gel sizing to identify those with the proper insert and orientation as in the map below.

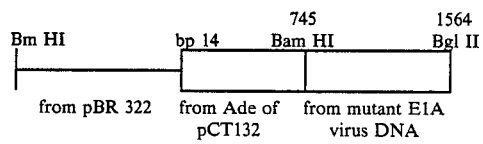

The ends are Bam HI/Bgl II ligated which is now a site recognized by Mbo I ($\downarrow$ GATC) but no longer by Bam HI (G $\downarrow$ GATCC) as Bgl II (A $\downarrow$ GATCT).

Such plasmids have been constructed and analyzed in transfected Hela cells. The mutant E1A gene products are capable of transactivation of transcription by other promoters including Ad3 E1A and Ad 3 hr 15 E1A promoters.

PHAGE EXAMPLE

A bacteriophage cloning of the mutant E1A genes could also be achieved using similar strategies for excision of the mutant E1A gene from purified viral (revertant) DNA. Cleavage of the viral DNA with HpaI (bp 95) and Gbl II (bp 1564) would excise the E1A promoter (Ad 3 hr 15 type) linked with the modified E1A coding sequences of the revertant. Studies in our laboratory have shown that DNA sequences upstream of the Hpa I site (bp 95) are not regions for regulated expression of the E1A gene. The Hpa I to Bgl II DNA fragment could be treated to place oligonucleotide linkers (Eco RI) on the ends for cloning between the left and right arms of a typical phage lambda vector.

Bacteriophage-mediated expression of (mutant) Ad3 E1A gene products is also feasible. This would require cloning of the cDNA frms of the E1A genes since bacterial cells lack the capacity for removal of introns. The cDNA would be synthesized using standard procedures with mRNA isolated from Ad 3 hr 15 revertant infected cells (recall that Ad 3 hr 15-dl 7 generates abundant E1A m RNA early and throughout infection). The 13S (small intron) mRNA would be the cDNA form of choice if products capable of transactivation are desired. Cloning of the cDNA into a bacteriophage expression vector such as phage lambda strain gt 11 would permit inducible expression of high levels of the mutant E1A proteins. Wild type Ad5 E1A proteins expressed in bacterial cells have been found to be active when microinjected into animal cells.

REFERENCES

Hearing, P. and Shenk, T. (1985), *Mol. Cell. Biol.,* 5, 3214–3221.

Kimelman, D., Miller, J. S., Porter, J. D., and Roberts, B. E. (1985), *J. Virol.* 53, 399–409.

Kosturko, L. D., et al. (1982), *J. Virol.* 43, 1132–1137.

Larsen, P. L., McGrane, M. M., Robinson, C. C., and Tibbetts, C. (1986), *Virology* 155, 148–159.

Maxam, A. M. and Gilbert, W. (1980), in Methods in Enzymology (eds. Grossman, L. and Moldave, K.), Vol. 65, 499-560 (Academic Press, New York).

Tibbetts, C. (1977), *J. Virol.*, 24, 564-579.

Tibbetts, C., Larsen, P., and Jones, S. M. (1986), *J. Virol.*, 57, 1055-1064.

Weeks and Jones (1983), *Mol. Cell. Biol.*, 3, 1222-1234.

We claim:

1. An isolated functional mutated E1A gene of human adenovirus subgroup B:1 having a modified autorepression functional domain including an in frame deletion in the region corresponding to the adenovirus wild type 3 (Ad3) DNA sequence between nucleotides 956 and 1024, said modified autorepression domain upon expression producing E1A products which stimulate in trans without net repression of an Ad3 promoter of the adenovirus subgroup B:1 E1A gene.

2. The mutated E1A gene of claim 1 in which the modification in said autorepression domain consists of an in frame deletion of from 27 to 69 base pairs (bp) between nucleotides 956 to 1024.

3. The mutated E1A gene of claim 2 in which said in frame deletion is a 27 bp deletion corresponding to the wild-type Ad3 DNA sequence starting with nucleotide 974 and ending with nucleotide 1000.

4. The mutated E1A gene of claims 1, 2, or 3 in which the mutated gene is derived from human adenovirus type 3 (Ad3).

5. The mutated E1A gene of claim 2 in which said gene is in the viral genome of a replicable virus of human adenovirus type 3 (Ad3).

6. The mutated E1A gene of claim 1 in which said gene is in the viral genome of a replicable virus of human adenovirus subgroup B.

7. A DNA expression vector containing the isolated mutated gene of claim 1 in which said gene is under control of an Ad3 E1A promoter of the human adenovirus subgroup B:1.

8. An expression vector containing the isolated mutated gene of claim 1 in which the E1A promoter of said expression vector comprises a transcriptional regulator followed in tandem by a duplicate thereof, said regulator responding to Ad3 E1A wild-type products to repress expression of the E1A gene and responding to the E1A products of the mutated gene to enhance expression of the mutated E1A gene products.

9. The expression vector of claim 9 in which said vector is a plasmid.

10. The expression vector of claim 9 in which said vector is a phage.

11. The mutated gene of claims 1, 2, or 3 in which said gene is derived from the Ad3 mutant virus identified as Ad 3 hr 15.

12. The mutated gene of claim 8 in which both said gene and said transcriptional regulator are derived from the Ad3 mutant virus identified as Ad 3 hr 15.

* * * * *